US008820930B2

(12) United States Patent
Fateh

(10) Patent No.: US 8,820,930 B2
(45) Date of Patent: Sep. 2, 2014

(54) SYSTEM, METHOD, AND APPARATUS FOR AMBLYOPIA AND OCULAR DEVIATION CORRECTION

(71) Applicant: Atheer, Inc., Mountain View, CA (US)

(72) Inventor: Sina Fateh, Sunnyvale, CA (US)

(73) Assignee: Atheer, Inc., Mountain View, CA (US)

( * ) Notice: Subject to any disclaimer, the term of this patent is extended or adjusted under 35 U.S.C. 154(b) by 0 days.

(21) Appl. No.: 13/775,042

(22) Filed: Feb. 22, 2013

(65) Prior Publication Data

US 2013/0162944 A1 Jun. 27, 2013

Related U.S. Application Data

(62) Division of application No. 12/517,167, filed as application No. PCT/US2007/086413 on Dec. 4, 2007, now Pat. No. 8,454,166.

(60) Provisional application No. 60/876,660, filed on Dec. 22, 2006, provisional application No. 60/872,836, filed on Dec. 4, 2006.

(51) Int. Cl.
*A61B 3/06* (2006.01)
*A61B 3/10* (2006.01)
*A61B 3/08* (2006.01)
*A61B 3/00* (2006.01)
*A61H 5/00* (2006.01)

(52) U.S. Cl.
CPC ... *A61B 3/00* (2013.01); *A61B 3/10* (2013.01); *A61B 3/08* (2013.01); *A61H 5/00* (2013.01)
USPC .......................................... 351/205; 351/246

(58) Field of Classification Search
CPC .............. G06F 3/013; G02B 2027/011; G02B 2027/0178; G02B 26/101; G02B 27/01; G02B 27/017; H04N 13/044; H04N 13/0468
USPC .......... 351/246, 201, 200, 205, 211, 212, 237
See application file for complete search history.

(56) References Cited

U.S. PATENT DOCUMENTS 4,896,959 A 1/1990 O'Brien
5,094,521 A 3/1992 Jolson et al.
(Continued)

FOREIGN PATENT DOCUMENTS

KR 1020040047785 5/2004

OTHER PUBLICATIONS

International Search Report and Written Opinion mailed Jun. 30, 2009, for International Application No. PCT/US2009/000251 filed Jan. 14, 2009.
Co-pending U.S. Appl. No. 12/517,167 by Fateh, S. filed Jun. 1, 2009, issued as U.S. Patent No. 8,454,166 on Jun. 4, 2013.
Co-pending U.S. Appl. No. 13/775,025 by Fateh, S. filed Feb. 22, 2013.

(Continued)

*Primary Examiner* — Hung Dang
(74) *Attorney, Agent, or Firm* — Perkins Coie, LLP

(57) ABSTRACT

Systems, methods, and apparatuses for amblyopia and ocular deviation correction, as well as visual interfaces, are disclosed. In one aspect, embodiments of the present disclosure include a system for amblyopia correction, the system includes, an image processing unit to identify a set of image parameters and, when, in operation, the image processing unit modifies a source visual content based on one or more of the set of image parameters to generate visual content and a visualization unit coupled to the image processing unit operable to receive visual content from the image processing unit, the visualization unit having a screen, when, in operation, the screen displays the visual content.

22 Claims, 10 Drawing Sheets

(56) References Cited

U.S. PATENT DOCUMENTS

| | | | |
|---|---|---|---|
| 5,920,374 A * | 7/1999 | Vaphiades et al. | ............ 351/237 |
| 6,260,970 B1 | 7/2001 | Horn | |
| 6,364,486 B1 | 4/2002 | Ball et al. | |
| 6,402,320 B1 | 6/2002 | Borchert | |
| 6,409,513 B1 | 6/2002 | Kawamura et al. | |
| 6,511,175 B2 | 1/2003 | Hay et al. | |
| 7,004,912 B2 | 2/2006 | Polat | |
| 7,326,060 B2 | 2/2008 | Seiller et al. | |
| 7,549,743 B2 | 6/2009 | Huxlin et al. | |
| 8,066,372 B2 | 11/2011 | Cooperstock et al. | |
| 8,454,166 B2 | 6/2013 | Fateh | |

OTHER PUBLICATIONS

Restriction Requirement mailed Mar. 26, 2012, for U.S. Appl. No. 12/517,167 by Fateh, S. filed Jun. 1, 2009.

Notice of Allowance mailed Nov. 15, 2012, for U.S. Appl. No. 12/517,167 by Fateh, S. filed Jun. 1, 2009.

Non-Final Office Action mailed Aug. 13, 2013 for U.S. Appl. No. 13/775,025 by Fateh, S. filed Feb. 22, 2013.

Notice of Allowance mailed Sep. 19, 2013, for U.S. Appl. No. 13/775,025 by Fateh, S., filed Feb. 22, 2013.

Non-Final Office Action mailed Mar. 7, 2014 for U.S. Appl. No. 13/775,025 by Fateh, S. filed Feb. 22, 2013.

* cited by examiner

SYSTEM, METHOD, AND APPARATUS FOR AMBLYOPIA AND OCULAR DEVIATION CORRECTION

CLAIM OF PRIORITY

This application is a U.S. Divisional Application of U.S. patent application Ser. No. 12/517,167, filed Jun. 1, 2009, now U.S. Pat. No. 8,454,166 which is a National Stage Application of International Application No. PCT/US2007/86413, filed Dec. 4, 2007, which claims the benefit of U.S. Provisional Application No. 60/876,660, filed Dec. 22, 2006 and U.S. Provisional Application No. 60/872,836, filed Dec. 4, 2006 all of which are hereby incorporated by reference in their entirety.

TECHNICAL FIELD

The present disclosure relates generally to non-invasive therapy of visual disorders, in particular, to facilitating treatment/correction for amblyopia and ocular deviation whilst a user is viewing visual content.

BACKGROUND

Amblyopia, commonly known as lazy eye, is one of the most common causes of visual impairment in children. The majority of the clinical investigations attribute amblyopia to the brain's preference for a dominant eye over a weak eye. The condition often persists into adulthood and bears the risk of bilateral vision impairment and even blindness. In fact, amblyopia has been reported as the leading cause of vision loss in one eye for the 20-70 year old age group, indicating a need to improve detection as well as treatment for the condition.

When diagnosed in children, the condition has traditionally been treated with occlusion therapy that excludes or reduces the vision in the dominant eye. Occlusion therapy typically requires the patient to use an eye patch that completely or partially covers the dominant eye. Compliance with occlusion therapy, however, has been problematic because the patients are typically no older than the age of seven. These young patients are unlikely to comply with the therapy for a number of reasons including personal distaste, skin irritation, cosmetic embarrassment, and other social and psychological factors.

An alternative treatment that has been relied upon to treat amblyopia is therapy using a cycloplegic drug known as atropine. Atropine functions by dilating the pupils and blurring the image seen through the dominant eye. Atropine addresses the low compliance rate for occlusion therapy but drug therapy progresses slower than occlusion therapy and paralyzes a key optical function in the dominant eye for an extended period of time.

Although occlusion therapy and atropine may improve visual acuity for patients, the visual gains are not guaranteed to remain stable and often regress when therapy ceases. Further, until a recent National Eye Institute study was published showing that many children from age seven through 17 with amblyopia may benefit from treatment, it was commonly believed that amblyopia is untreatable for anyone beyond the age of seven. Therefore, neither occlusion therapy nor atropine has been effectively used to treat patients over the age of seven.

In a human eye, there are six external muscles that move both eyes together in synchronized motion. Ocular deviation occurs when one or both eyes do not move normally, causing abnormal visual reception. As a result, a patient may experience one or more symptoms or visual impairments including diplopia where the patient has double vision or strabismus, also known as "cross-eyes," where the patient's eyes do not look at the same point at the same time. Ocular deviation may result from ocular or neurological damage including ocular nerve palsy, vascular disease, thyroid disease, multiple sclerosis, myasthenia gravis, traumatic brain injury, stroke, facial fracture, or eye trauma.

Although a majority of patients whose condition results from trauma such as brain injury or stroke recover within 12 months, proper vision assistance is critical to recovery. Traditional therapies for ocular deviation include patching one eye to eliminate the image received in that eye and rendering the patient monocular, and using prisms to fuse the images received by both eyes. Patching, however, may be uncomfortable and causes cosmetic concerns. Prism, on the other hand, can create other problems such as eye strain when the prismatic lenses used are improperly adjusted or unstable.

Binocular vision (binocular refers to two eyes) is the result of the alignment of the eyes and the unification of their respective views of the environment. Binocular vision provides depth evaluation and stereoscopic vision. The binocular vision could be affected by deficiencies such as, amblyopia (or, reduction of vision in one eye), strabismus deviation of one eye, diplopia (or, a condition where a single object is seen in double), accommodation deficit (or, a condition where the eye is not able to obtain clear image of near object), and/or convergence and fusion insufficiency (or, inability to maintain superimposition of 2 images).

In addition to providing stereopsis and an improved field of vision, benefits of having good binocular vision include the ability to perform advanced visual tasks. Binocular weaknesses such as convergence and fusion insufficiency (inability to maintain superimposition of 2 images) reduce visual performance.

SUMMARY OF THE DESCRIPTION

Systems, methods, and apparatuses for amblyopia, ocular deviation, and binocular vision diagnosis and correction are described here. Some embodiments of the present disclosure are summarized in this section.

In one aspect, embodiments of the present disclosure include a method, which may be implemented on a system, of amblyopia diagnosis and/or treatment. The treatment method includes, measuring a first visual function of a first eye of a user and defining a first set of image parameters based on the first visual function of the first eye. The treatment method further includes, in one embodiment, receiving source visual content and generating a first visual content for the first eye by processing the source visual content based on at least one of the first set of image parameters.

One embodiment further includes enhancing the source visual content to generate the first visual content responsive to determining that the visual function of the first eye is deficient and reducing the source visual content to generate the first visual content responsive to determining that the visual function of the first eye is non-deficient. Deficiency of the first eye can include the conditions of, lack of visual acuity, lack of contrast sensitivity, lack of spatial frequency, lack of contour detection, lack of edge detection, stereovision, and mis-orientation.

One embodiment further includes, evaluating visual progress of the first eye via re-measuring an updated first visual function of the first eye and redefining an updated first set of image parameters based on the updated first visual function to generate an updated first visual content by processing the source visual content based on at least one of the updated first set of image parameters.

One embodiment further includes measuring a second visual function of a second eye of a user and defining a second set of image parameters based on the second visual function of the second eye. The treatment method further includes, in one embodiment, receiving source visual content and generating a second visual content for the second eye by processing the source visual content based on at least one of the second set of image parameters.

In a further aspect, embodiments of the present disclosure include a system for amblyopic diagnosis and/or correction. The system may include, an image processing unit to identify a set of image parameters and, when, in operation, the image processing unit modifies a source visual content based on one or more of the set of image parameters to generate visual content and/or a visualization unit coupled to the image processing unit operable to receive visual content from the image processing unit, the visualization unit having a screen, when, in operation, the screen displays the visual content.

The image processing unit can be coupled to a content source, when, in operation, the content source provides the image processing unit with the source content. The content source may be a video game, a television, a computer, a video source, a digital camera, a camcorder, and/or a portable media player. The visualization unit is, in one embodiment, a monocular head mounted unit and/or a binocular head mounted unit.

In a yet further aspect, embodiments of the present disclosure include head-mountable display apparatus for ocular deviation diagnosis and/or correction. The apparatus includes, a first optical lens operatively configured for adjustable rotational movement and/or adjustable vertical movement. One embodiment includes a first display screen optically coupled to the first optical lens. The first display screen can be operatively configured for the adjustable rotational movement and/or the adjustable vertical movement. The apparatus may further include, in one embodiment, a first adjustment system coupled to the first optical lens and the first display screen. The first adjustment system is, in one embodiment, operatively configured for adjustable rotational movement and/or the adjustable vertical movement.

The adjustable rotational movement and the adjustable vertical movement are typically determined based on a deviation of a first line of sight of a first eye from a predetermined axis. In some embodiments, the predetermined axis is determined from on a second line of sight of a second eye. One embodiment further includes a measuring means to track the amount and deviation of the first line of sight of the first eye from the predetermined axis.

In one embodiment, the apparatus further includes, a second optical lens operatively configured for one or more of rotational movement and vertical movement and/or a second display screen optically coupled to the second optical lens. The second display screen is, in one embodiment, operatively configured for the one or more of the rotational movement and the vertical movement. The apparatus may further include, a second adjustment system coupled to the second optical lens and the second display screen. The second adjustment system may be operatively configured for the rotational movement and/or the vertical movement. The rotational movement and the vertical movement are independent of the adjustable rotational movement and the adjustable vertical movement, respectively.

In one aspect, embodiments of the present disclosure include a method, which may be implemented on a system, of ocular deviation diagnosis and/or correction. The correction method includes, identifying a first line of sight of a first eye of a user and/or identifying a second line of sight of a second eye of the user. A deviated eye among the first eye and the second eye can be identified based on the first line of sight and the second line of sight. An amount and type of eye deviation of the deviated eye can further be determined to adjust a position of a display for presenting visual content to the deviated eye. One embodiment further comprises, re-evaluating the amount and the type of eye deviation of the deviated eye and re-adjusting the position of the display.

In one aspect, embodiments of the present disclosure include a method, which may be implemented on a system, of binocular vision diagnosis and/or correction. The method includes, presenting a first image to a first eye of a user and presenting a second image to a second eye of a user. One embodiment further comprises, simultaneously displacing the first image and the second image. For example, the first image and the second image can be moved away from one another and/or towards one another. A unilateral displacement of one image can be used to measure the deviation of one eye.

The present disclosure includes methods and systems which perform these methods, including processing systems which perform these methods, and computer readable media which when executed on processing systems cause the systems to perform these methods.

Other features of the present disclosure will be apparent from the accompanying drawings and from the detailed description which follows.

DETAILED DESCRIPTION

Figure 1:
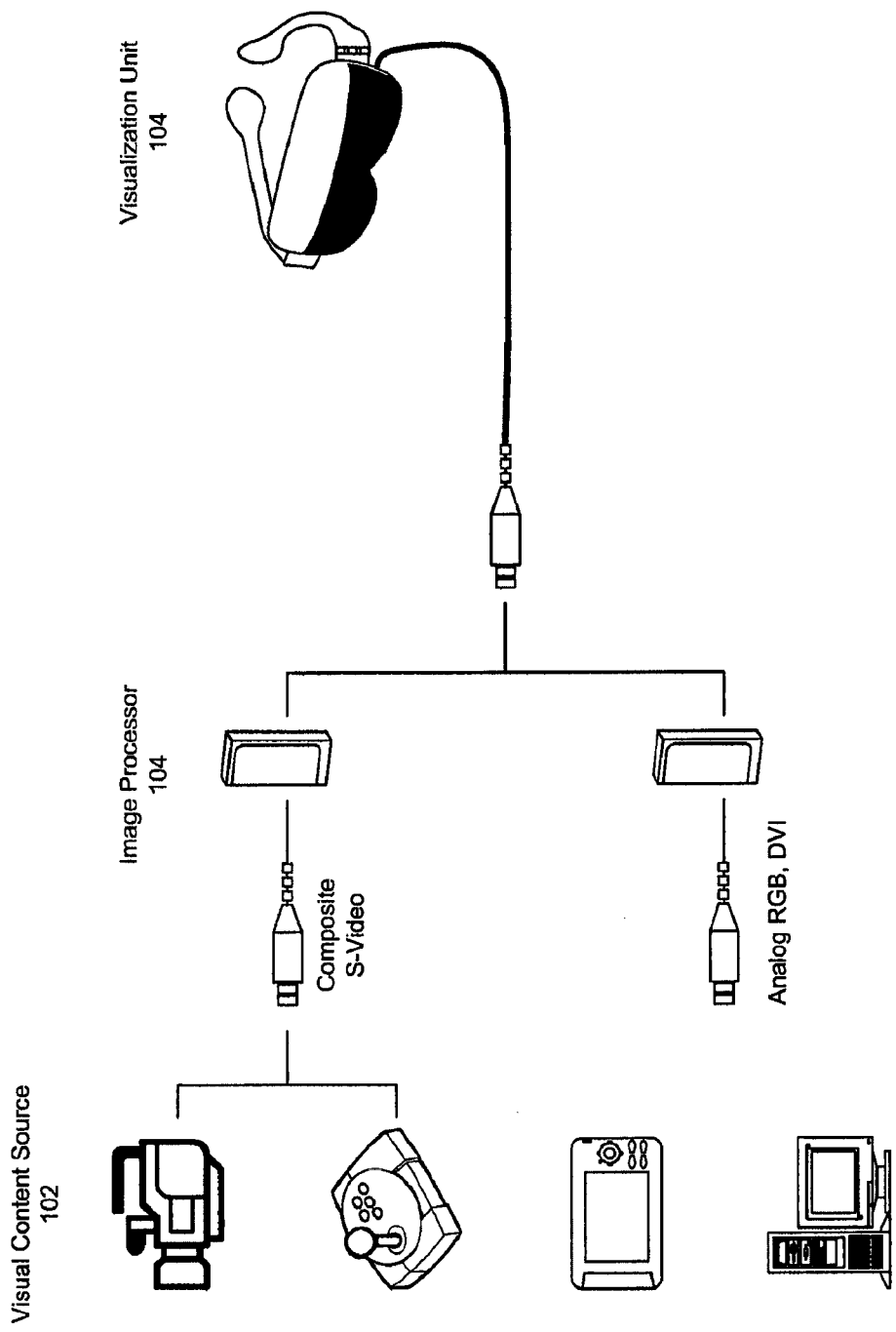
FIG. 1 depicts an example of a system for modifying visual content to facilitate amblyopia treatment and/or correction.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

Embodiments of the present disclosure include systems, methods, and apparatuses for amblyopia and ocular deviation treatment and/or correction.

One embodiment of the present disclosure includes a system for treating and/or improving the conditions of amblyopia in the affected eye.

Amblyopia (also referred to as 'lazy eye') is the loss of visual function of one or more eyes with neither detectable pathology nor structural abnormality. The loss of visual function can be attributed to the preference of the brain for one eye over another. The preference may be due to, for example, during the infancy, an area of the visual cortex was deprived of adequate visual inputs. In some situations, misalignment of the eyes (strabismus) may cause amblyopia by causing the brain to receive substantially different images from the eyes. When this occurs, the brain can suppress the blurrier image, eventually leading to amblyopia.

Another common cause of amblyopia is anisometropia, when there is a difference in the refractive states between two eyes. The difference in refractive states cause different images from the two eyes to be presented to the brain where one may be suppressed, causing the eye to become amblyopic. Additional, cataract, or clouding of the lens of an eye can cause a blurry image further leading to amblyopia of the cataract eye. Conceptually, treatment/therapy of amblyopia includes depriving the visual cortex corresponding to the unaffected eye of stimulation while supplying the visual cortex corresponding to the amblyopic eye with ample stimulation.

The system for amblyopia treatment can include an image processor for modifying visual content to be presented to the amblyopic eye. For example, spatial frequency and contrast of visual content to be presented to the affected can be enhanced to improve cortical perception. The degree of image enhancement is typically determined from the degree of visual deficiency of the amblyopic eye. In particular, visual functions of the amblyopic eye can be measured for determination of image parameters for which the image modification can be based on.

Image processing for amblyopic treatment can be performed on various types of visual content including but not limited to, television content, video game content delivered via portable devices, television sets, and/or computers/laptops, computer-based content, cell phone content, etc. In some instances, visual content to be presented to the un-affected eye (e.g., the eye that is non-deficient relative to the amblyopic eye) is modified as well. For example, spatial frequency/contrast and/or other image parameters of the content to be presented to the un-affected eye can be reduced relative to the enhanced image to decrease cortical stimulations from the un-affected eye.

In some instances, the system includes a visualization unit (e.g., head-mountable display) coupled to a visual content source. The visualization unit may include the image processor for modifying visual content. A user may view the content source through the display lens of the visualization unit. Since the images presented through the content source are modified (e.g., enhanced and/or reduced), the user receives therapy for amblyopia whilst performing everyday tasks (e.g., watching TV, doing homework, working on a computer, browsing the web, playing video games, etc.). The image processing performed on the source visual content is typically adjustable since after the user begins therapy, the amblyopic eye may begin to demonstrate improvements in visual functions. Visual tests can be performed periodically (automatically and/or manually) for adjustments of the parameter settings in the image processing.

One embodiment of the present disclosure includes a method and apparatus for ocular deviation correction.

When a patient suffers from ocular deviation, the two eyes are not pointing at a same point in space. A human eye typically has six external muscles that move the eyes in conjunction. When one or more of these external muscles are impaired, a misalignment between lines of sights may occur between the two eyes. Misalignments may also occur due to ocular damage, neurological damage, and/or other health disorders. Causes of ocular deviation can include but are not limited to, ocular nerve palsy, vascular disease or hypertension, thyroid disease, multiple sclerosis, myasthenia gravis, brain injury, stroke facial fracture, and/or eye trauma. In some cases, ocular deviation causes diplopia, or seeing two images of the same view. The two images can appear horizontal, vertical, or oblique to each other.

In one embodiment, the apparatus for ocular deviation therapy includes a moveably adjustable display and/or lens system. The display is, in some instances, a head-mountable display. The display and/or lens can be adjusted such that they are aligned with the deviated eye. Based on the amount of deviation and the type of deviation, the corresponding display and/or lens can be moved in front of the line of sight (e.g., visual axis) of the deviated eye. In some embodiments, the amount of deviation and/or the type of deviation are measured to determine displacement of the display/lens system. By presenting an image aligned to the deviated eye and another image aligned to the un-affected eye, the brain is able to fuse the two images into one stereoscopic image. Typically, by progressively reducing displacement of the display/lens system, the deviated eye will gradually become aligned with the other eye.

The techniques involved in the disclosure of amblyopia and ocular deviation therapy/correction are not limited to treatment of amblyopic and/or ocular deviation, but in essence, are contemplated to be broadly applicable to treatment of any ocular disorder and/or malfunction that involve diminished visual functions in one or more eyes and/or one eye that is deviated from the other, and are considered to be within the scope of the novel disclosure.

Amblyopia Diagnosis/Therapy

FIG. 1 depicts an example of a system 100 for modifying visual content to facilitate amblyopia treatment and/or correction.

The example system 100 of FIG. 1 includes a visual content source 102, an image processor 104, and/or a visualization unit 106. The visual content source 102 can include any combination of one or more devices and/or systems that is able to generate and/or playback visual content (e.g., image content, video content), including by way of example but not limitation, digital cameras, camcorders, game machines (e.g., PlayStation I, II, III, Xbox, Nintendo, etc.), media players, a portable phone (e.g., cell phone, Blackberry, Treo, iPhone, and/or any other portable devices with imaging and video capabilities), and/or a computing devices (e.g., a desktop computer, a laptop computer, etc.).

In some instances, the image processor 104 is externally coupled to the visual content source 102. As shown in the example of FIG. 1, the image processor 104 is couple-able the visual content source 102 via an S-video connection, composite video, analog RBG, VGI, HDMI, and/or a DVI connection. In some embodiments, the image processor 104 is internal to the visual content source 102 for performing image processing on the source visual content. In some embodiments, the image processor 104 is coupled to the visual content source 102 wirelessly. For example, the image processor 104 can receive visual content from the source 102 via a wireless network such as, a Local Area Network (LAN), Wireless Local Area Network (WLAN), a Personal area network (PAN), a Campus area network (CAN), a Metropolitan area network (MAN), a Wide area network (WAN), a Wireless wide area network (WWAN), Global System for Mobile Communications (GSM), Personal Communications Service (PCS), Digital Advanced Mobile Phone Service (D-Amps), Wi-Fi, Fixed Wireless Data, or any other wireless data networks.

The visualization unit 106 is, in one embodiment, a head-mountable display couple-able to the image processor 104 and/or the visual content source 102. The visualization unit typically includes two displays suitable for presenting visual content to each eye and can be, by way of example but not limitation, any display/lens combination system, video eyewear, ear-mountable display, head-mountable display, with image/video display capabilities. The visual content presented to each eye may be different or similar. For example, the image processor 104 can generate two visual content from the source visual content to be presented to different eyes, for example, for therapeutic purposes to facilitate treatment of an eye disorder/malfunction. When the visualization unit is in operation, the two images received from the image processor 104 can be separately displayed to each eye.

Figure 2:
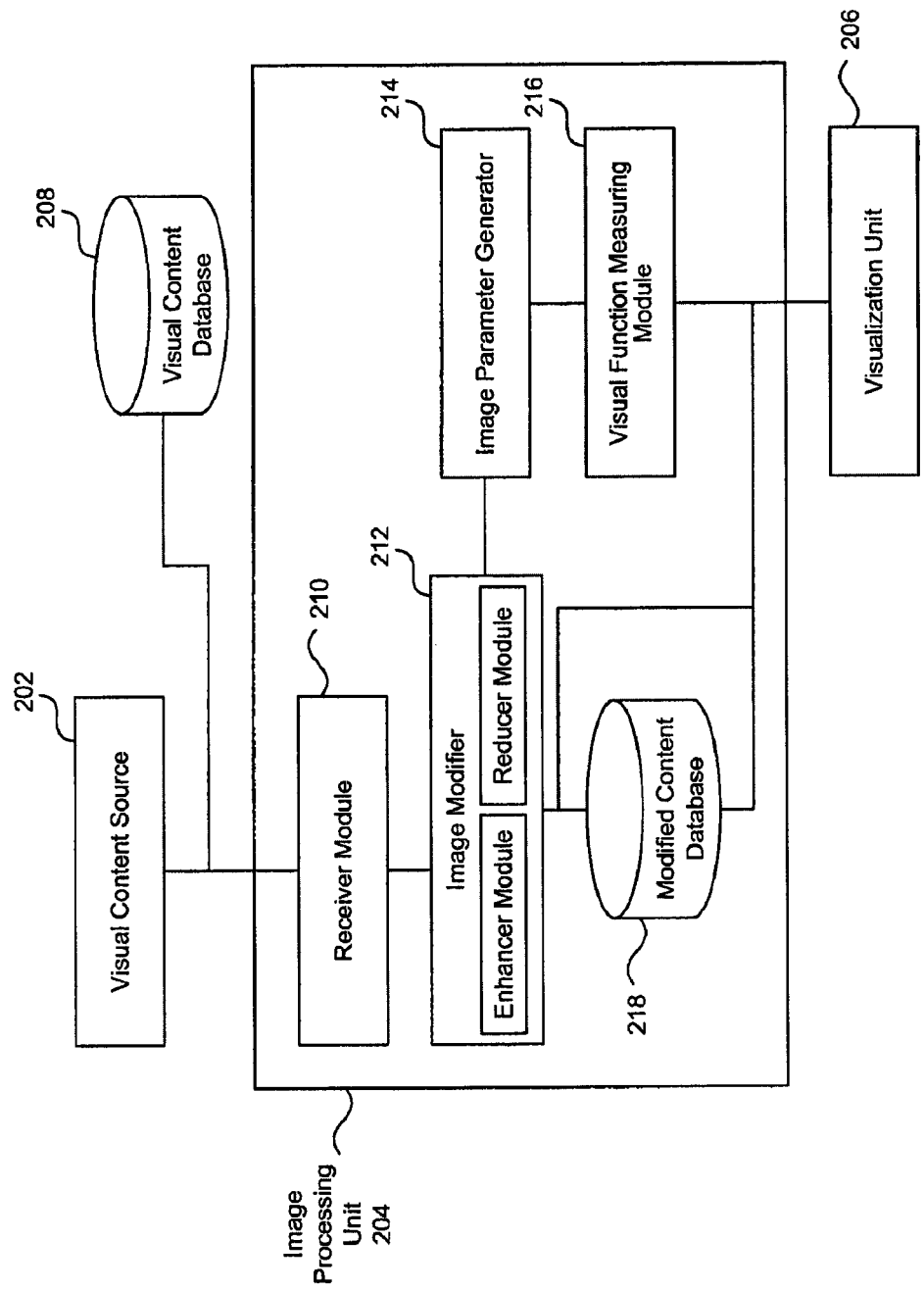
FIG. 2 depicts an example of a block diagram of an image processing unit for modifying visual content to facilitate amblyopia treatment and/or correction.

FIG. 2 depicts an example of a block diagram of an image processing unit 204 for modifying visual content to facilitate amblyopia treatment and/or correction.

The image processing unit 204 in the example of FIG. 2 includes a receiver module 210, an image modifier 212 having an enhancer module and a reduction module, a modified content database 218, an image parameter generator module 214, and/or a visual function measuring module 216. Additional or less modules may be included in the image processing unit 204. The image processing unit 204 may be coupled to one or more of a visual content source 202, a visual content database 208, and/or a visualization unit 206. In some instances, the image processing unit 204 is internal to the visual content source 202. In some embodiments, the image processing unit 204 is internal to the visualization unit 206.

The visual content database 208 and the modified content database 218 can store software, descriptive data, images, system information, drivers, and/or any other data item utilized by components of the visual content source 202 or image processing unit 204 for operation including archived video and/or image files. In particular, the modified content database 218 can store visual content that has been modified by the image modifier 212. Content stored in the database 218 can be accessible by the visualization unit 206 and/or the image modifier 212.

The databases 208 and 218 may be managed by a database management system (DBMS), for example but not limited to, Oracle, DB2, Microsoft Access, Microsoft SQL Server, PostgreSQL, MySQL, FileMaker, etc. The visual content database 208 can be implemented via object-oriented technology and/or via text files, and can be managed by a distributed database management system, an object-oriented database management system (OODBMS) (e.g., ConceptBase, FastDB Main Memory Database Management System, JDO-Instruments, ObjectDB, etc.), an object-relational database management system (ORDBMS) (e.g., Informix, OpenLink Virtuoso, VMDS, etc.), a file system, and/or any other convenient or known database management package.

The receiver module 210 can be any combination of software agents and/or hardware modules that receives visual content, as implemented by any known and/or convenient manner. For example, visual content may be received via a video connector (e.g., DVI, HDMI, composite, S-video, PAL, VGA, etc.) and/or via a wireless connection established with the visual content source 202.

The image modifier 212 is any combination of software agents and/or hardware components able to modify image content. In one embodiment, the image modifier includes an enhancement module and a reduction module for enhancing and reducing visual content, respectively. The image modification is performed by one or more known and/or convenient image processing techniques including but not limited to, geometric transformations, color corrections (e.g., brightness and/or contrast adjustments, quantization, conversion to a different color space), registration (e.g., alignment of two or more images), interpolation, de-mosaicing, segmentation, image editing, image scaling, image cropping, de-convolution, edge preserving smoothing, edge enhancement, perspective correction and distortion correction, image orientation adjustment, classification, noise removal, feature extraction, and/or pattern recognition, etc.

In some embodiments, the image modifier 212 as shown in the example of FIG. 2 can include one or more modules having any combination of software and hardware components to facilitate image capture of still and/or moving objects, with or without processing of the image captured. In some instances, some of the functionalities of the image modifier 212 can be used for capturing video images. For example, the imaging device, can be, but is not limited to a webcam, a digital single-lens reflex camera, a digital camera (e.g., a compact digital camera, a bridge camera, etc.), a rangefinder camera, a film camera, a movie camera, and/or a video camera. Although one image modifier is shown in the example shown in the figure, the image modifier 212 can be a combination of one or more cameras of the same or differing types, for example, pointed towards different directions to capture images/videos.

Additional functionalities, such as image processing functions, audio recording functions, video/image editing functions, taping/playback functions, live preview functions, may be provided by the image modifier 212 without deviating from the spirit of the novel art of this disclosure. The image modifier 212, can include, one or more of, or any portion of the one or more of the above described functions, without deviating from the spirit of the novel art of the disclosure.

The image parameter generator 214 is any combination of software agents and/or hardware modules able to generate one or more image parameters based on input data (e.g., input data related to visual functions of a user). The image modifier 212 is, in some embodiments, coupled to the image parameter generator 214. The image parameter generator provides the image modifier 212 with one or more parameters with which to modify the source visual content. The image parameters can include, by way of example, but not limitation, contrast, brightness, color (e.g., color map, color depth, color adjustments), spatial frequency, sharpness, size, noise, motion, special effects, and/or orientation. In some embodiments, the image parameter generator is internal to the image modifier.

The visual function measuring module 216 can be any combination of software agents and/or hardware modules able to assess the vision functions of one or more eyes of a user. Assessment of human visual functions can include, but are not limited to, visual acuity, contrast sensitivity, spatial frequency, contour and edge detection capabilities, stereovision, and/or orientation discrimination abilities. Visual function measurements can include visual tests including, but not limited to, pupil dilation, hand-held slit lamp examination, ophthalmoscope examination of the retina, macula, and/or optic nerve, electrorectinogram (ERG), and/or visual evoked potential (VEP), etc. The visual function measuring module 216 can perform a pre-evaluation test and provide results of the assessed visual functions of one or more eyes of a user to the image parameter generator 214.

Based on the visual assessment of a user, the image parameter generator 214 determines one or more image parameters to be applied to visual content for enhancement or reduction purposes. For example, an enhancement parameter can be generated to enhance the spatial frequency and/or the contrast of a source visual content upon determining that a user eye has deficient visual capacities. The enhancement parameter is typically proportional to the amount of visual deficit. Similarly, a reduction parameter can be generated to reduce the spatial frequency and/or contrast of the source content for a non-deficient eye. The reduction parameter is also typically proportional to the visual strength of the non-deficient eye.

The image parameter generator 214 is, in some embodiments, internal to the visual function measuring module 216. In addition, the visual function measuring module can periodically perform vision assessments, for example, to determine whether visual functions of a defective eye has improved. In some embodiments, the improvement in eye functions can be quantified and utilized to generate updated sets of image parameters. The updated image parameters can be used to modify the source visual content such that they are suited for the improved eye. Assessment of vision functions can be performed automatically at predetermined intervals or be manually triggered, for example, by a user or by a supervisor.

The visual function measuring module 216 can be coupled to a visualization unit 206. Through the visualization unit 206, the visual function measuring module 216 is able to optically couple to the eye to perform assessment of vision functions of one or more user eyes. In some embodiments, the visual function measuring module is internal to the visualization unit 206.

The visualization unit 206 is, in one embodiment, a head-mountable display couple-able to the image modifier 212 and/or the visual content source 202. The visualization unit, typically includes two displays suitable for presenting visual content to each eye and can be by way of example but not limitation, any display/lens combination system, video eyewear, with image/video display capabilities. The visual content presented to each eye may be different or similar. For example, the image modifier 212 can generate two visual content from the source visual content to be presented to different eyes by sending the modified content to the visualization unit 206, for example, for therapeutic purposes to facilitate treatment of an eye disorder/malfunction. When the visualization unit 206 is in operation, the two images received from the image modifier 212 are presented separately to each eye.

In some embodiments, each component of the image processing unit 204 can be physically and/or functionally (e.g., hardware and/or software components) integrated with one or more of the other components. For example, one or more of the above described devices or any physical or functional portion of the one or more of the above-described devices can be integrated with the visual content source rather than externally coupled to the visual content source as illustrated in the example of FIG. 2.

Figure 3:
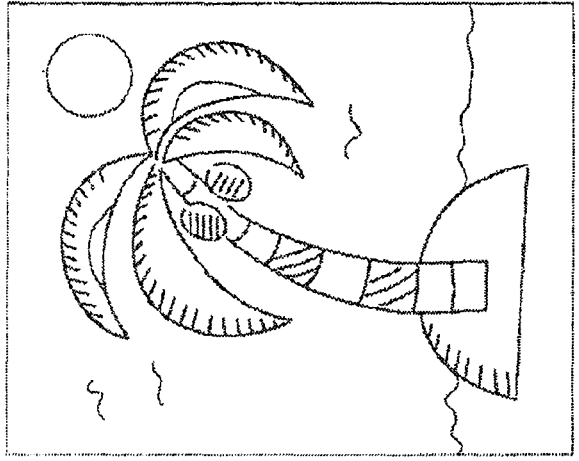
FIG. 3 illustrates an example of an enhanced image to be presented to a deficient eye and an example of a reduced image to be presented to a non-deficient eye for amblyopia treatment.
Figure 3:
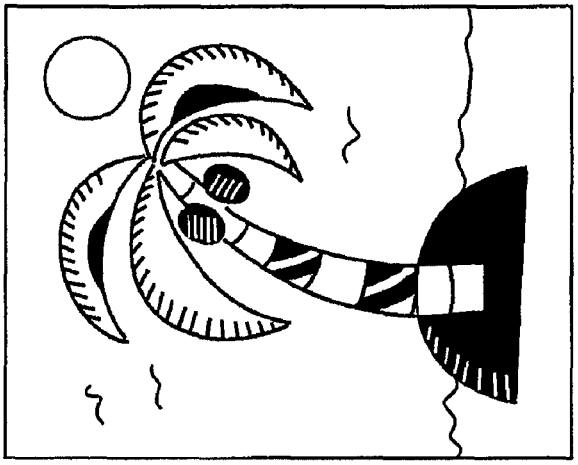
Figure 3:
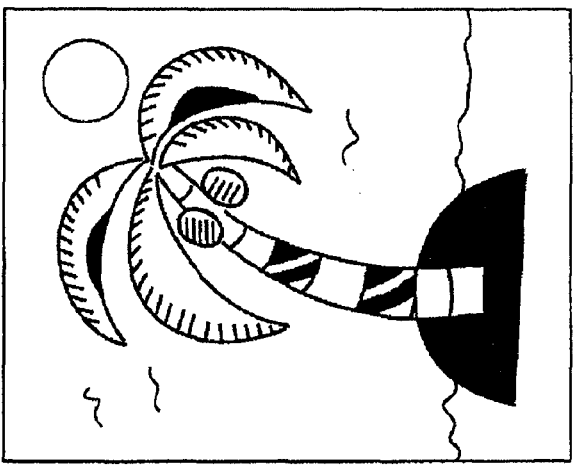

FIG. 3 illustrates an example of an enhanced image 304 to be presented to a deficient eye and an example of a reduced image 306 to be presented to a non-deficient eye for amblyopia treatment.

The original image 302 in the example of FIG. 3 can be modified (e.g., enhanced or reduced) and presented to an amblyopic eye and an un-affected eye, respectively. Based on image adjustment parameters determined from the degree of visual deficiency and visual strength, an enhanced image 304 and a reduced image can be generated 306, for example. As can be seen, the enhanced image 304 has sharpened contrast where as the reduced image 306 has reduced contrast from the original image 302. The enhanced image and the reduced image are typically generated such that they can be fused together at the cortex level to be perceived normally by the user.

Eye Deviation Diagnosis/Correction

Figure 4:
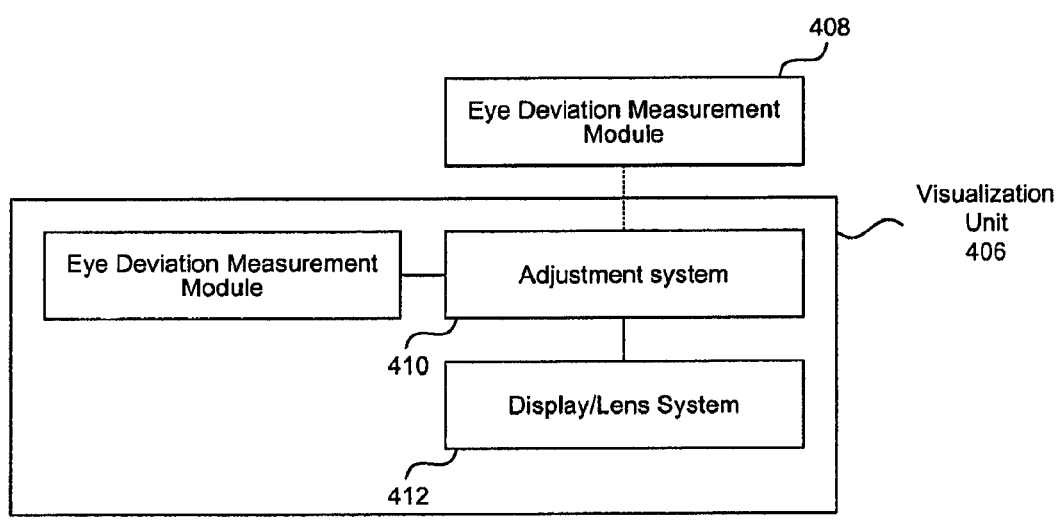
FIG. 4 depicts an example of a visualization unit that adjusts the position and/or the orientation of a display/lens system to facilitate ocular deviation treatment and/or correction.

FIG. 4 depicts an example of a visualization unit 406 that adjusts the positions of a display/lens system 412 to facilitate ocular deviation treatment and/or correction.

The visualization unit 406 can include any combination of software agents and/or hardware modules able to present visual content to one or more eyes of a user. For example, the visualization unit 406, can include two displays suitable for presenting visual content to each eye and can be, by way of example but not limitation, any display/lens combination system, video eyewear, with image/video display capabilities. The visual content presented to each eye may be different or similar. In the example of FIG. 4, the visualization unit 406 includes an eye deviation measurement module 408, an adjustment system 410, and a display/lens system 412.

The eye deviation measurement module 408 can include any combination of software agents and/or hardware modules able to identify eye deviation. The eye deviation measurement module 408, when, in operation, is optically coupled to the visualization unit 406 such that the user eyes are visible through the lens. The eye deviation measurement module 408 can then determine a line of sight in each of the user eyes, for example, and identify the deviated eye from the measurements. In one embodiment, the eye deviation measurement module 408 further evaluates the amount of deviation and/or the type of deviation (e.g., horizontal deviation, vertical deviation, rotational deviation, and/or tilt deviation). For example, two images can be sent to each eye on the visualization unit. If the two images are seen as two images, typically the user has eye deviation. The image positions can then be adjusted, for example, by adjusting the position of the display/lens position, until one image is seen. The position can be adjusted by another person or by the user. The amount of deviation can be determined by the amount of adjustment made until the user sees one image. The eye deviation measurement module is, in some embodiments, external to the visualization unit 406, as illustrated.

The adjustment system 410 is any combination of software agents and/or hardware components able to receive, process, and/or execute control signals governing movement/position adjustment of the display/lens system 412. For example, the adjustment system 410 can include an actuator (e.g., pneumatic, electric, motor, magnetic, piezoelectric, etc.) that, when in operation, controls the movement and/or positioning of the display/lens system 412. The adjustment system 410 is also manually controllable for positioning the display/lens system. The adjustment system 410 is, in some embodiments, operatively configured to displace the display/lens system horizontally, vertically, rotationally, and/or in a tilted fashion.

The adjustment system 410 is, in some embodiments, communicatively coupled to the eye deviation measurement system 408. The adjustment system 410 moveably adjusts the position of the display/lens system 412 based on the measurement results provided by the eye deviation measurement system 408. For example, if the eye deviation measurement system 408 determines that one user eye is deviated based on deviation of the line of sight of the eye from a predetermined axis, the adjustment system 410 can adjust the position of the display/lens system 410 for the deviated eye such that the display and/or lens is aligned with the deviated line of sight. In some instances, the predetermined axis is determined from the line of sight of the un-affected eye. In some embodiments, the adjustment system 410 is manually adjustable.

The distance between the eye and the display/lens system 412 is typically maintained by the adjustment system 410 while adjusting the position of the display/lens system 412 to prevent optical distortion. For example, the adjustment system 410 can have a circular movement path such that the radial distance to an eye is substantially the same during position adjustment. The display/lens system 412 typically includes one or more displays optically coupled to optical lenses (e.g., magnifying lens). In most instances, the system 412 includes two sets of displays coupled to lenses suitable for displaying visual content to each eye. According to embodiments of the present disclosure, each display/lens in the display lens system is individually controllable. For example, each set may have its corresponding adjustment system 410 such that the display/lens can be adjusted in position independent of the other display/lens.

Figure 5A:
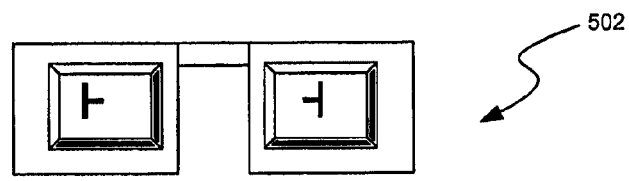
FIG. 5A is a diagrammatic example of viewing visualization content through a visualization unit for participating in an ocular deviation treatment/correction therapy session.

FIG. 5A is a diagrammatic example of viewing visualization content through a visualization unit for participating in an ocular deviation treatment/correction therapy session.

The visualization unit in the example of FIG. 5A includes two viewing areas. Each viewing area is suitable for displaying visual content to each eye. The visual content displayed in each viewing area can be individually modifiable. For example, the visual content displayed in each viewing area may have undergone differing image processing techniques. In addition, the display and/or lens associated with each viewing area may be individually adjustable in position, according to one embodiment.

Figure 5B:
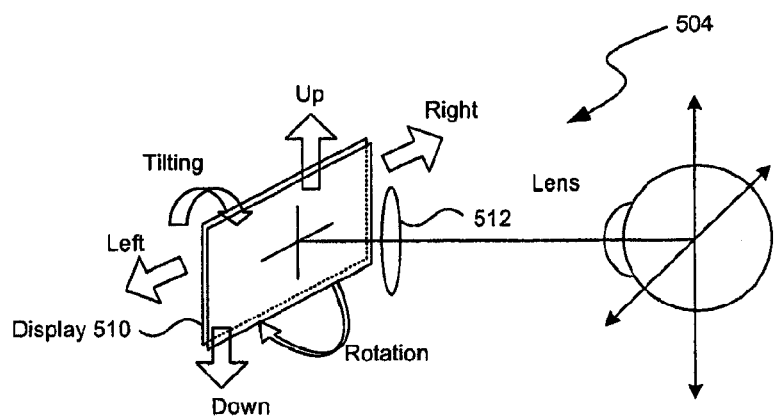
FIGS. 5B-C depict diagrammatic examples illustrating the position of a display and a lens of the visualization unit relative to an eye.
Figure 5C:
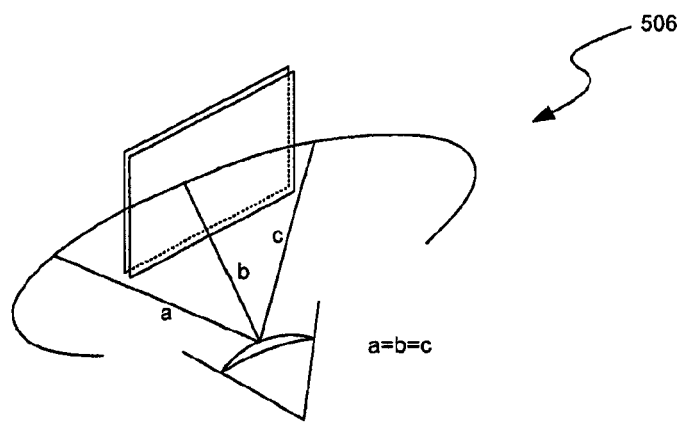

FIGS. 5B-C depict diagrammatic examples illustrating the position of a display 510 and a lens 512 of the visualization unit relative to an eye.

As shown in the example FIG. 5B, the display/lens system is able to move and/or rotate in various directions relative to a user eye. As illustrated, the display 510 and the lens 512 can be moved up, down, right, left, rotated, and/or tilted relative to the user eye. The example display/lens system illustrated in FIG. 5C depicts a circular pathway within which the display and/or lens moves. By keeping the display/lens system on a circular path, the distance (as illustrated by a=b=c) between the user eye and the display/lens system can be maintained, according to one embodiment of the present disclosure.

Figure 6A:
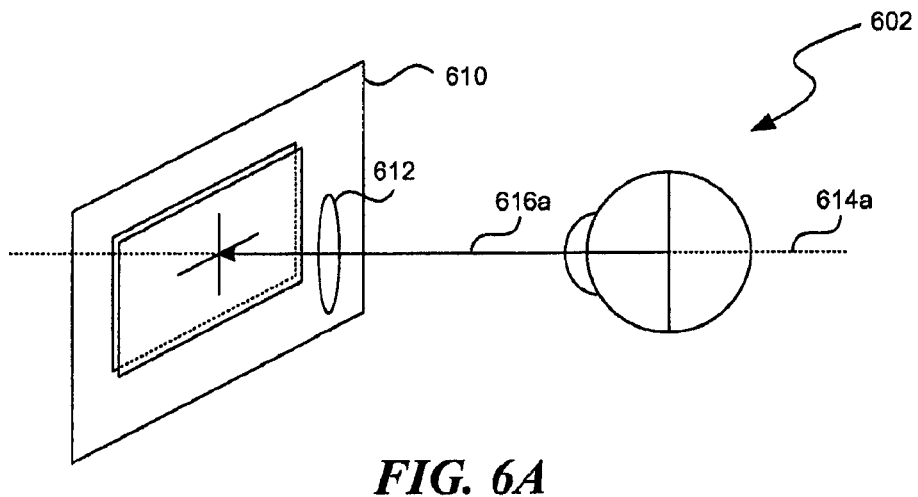
FIGS. 6A-C depict diagrammatic examples illustrating the adjustability of the display and the lens of the visualization unit relative to an eye for ocular deviation treatment and/or correction.
Figure 6B:
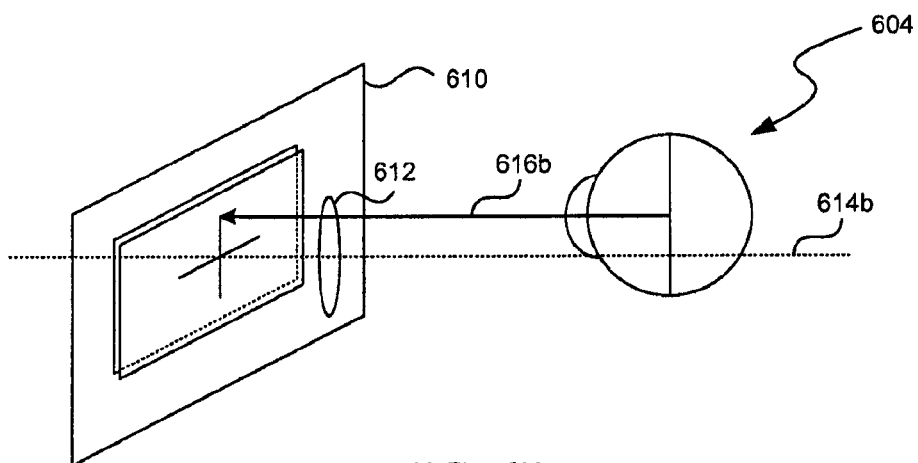
Figure 6C:
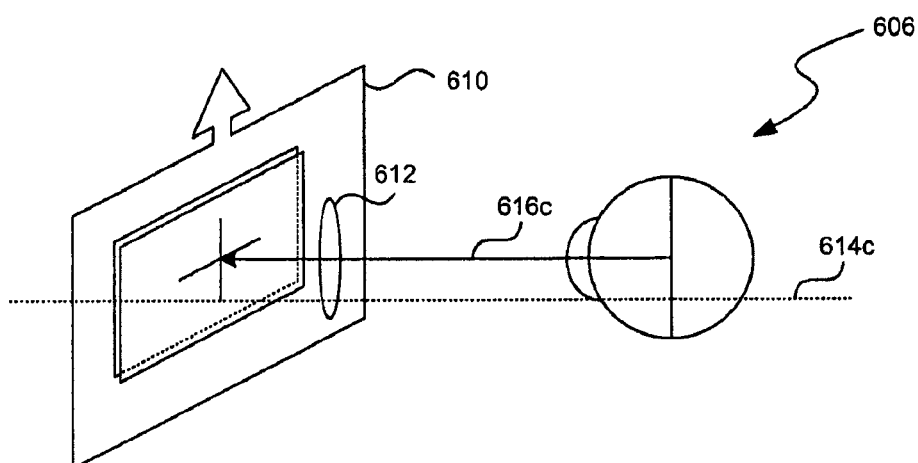

FIGS. 6A-C depict diagrammatic examples illustrating the adjustability of the display 610 and the lens 612 of the visualization unit relative to an eye for ocular deviation treatment and/or correction.

In the example of FIG. 6A, the position of an un-affected eye (e.g., non-deviated eye) relative to the display 610 and lens 612 system is illustrated. The line of sight 616A in this example is aligned with the display 610 and the lens 612 as can be seen by the overlapped line of sight 616A and a predetermined axis 614A. No adjustment of the display 610 or the lens 612 position is necessary in this case.

In the example of FIG. 6B, the position of a deviated eye relative to the display 610 and lens 612 system is illustrated. The line of sight 616B in this example is deviated from the predetermined axis 614B and the visual axis is vertically displaced from the center of the display 610 and lens 612. In this situation, as shown in the example of FIG. 6C, the display 610 and/or lens 612 can be moved vertically such that the line of sight 616C is aligned with the predetermined axis 614C such that the visual axis is aligned with the center of the display 610 and lens 612.

Binocular Vision Diagnosis/Treatment

Figure 7:
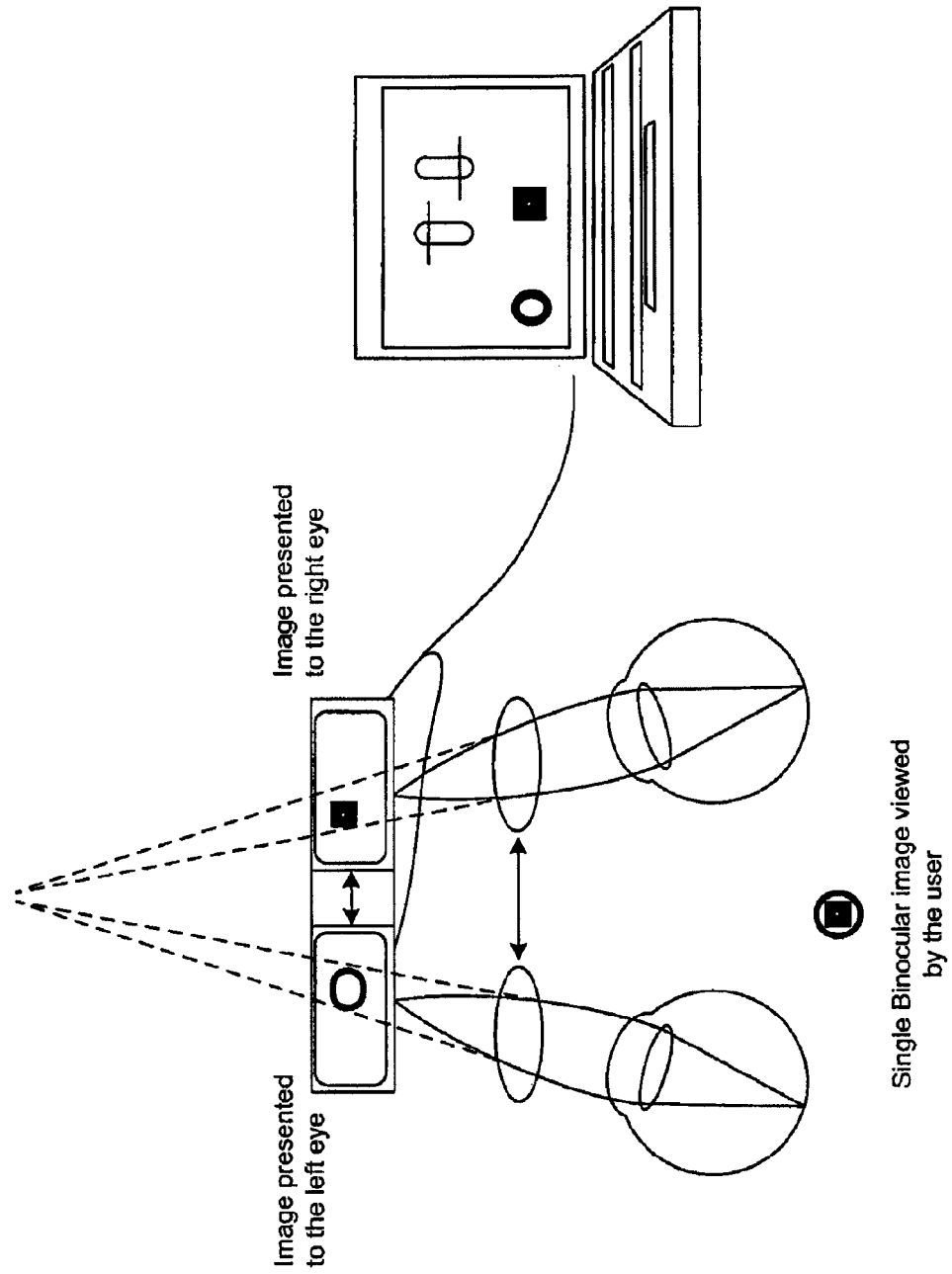
FIG. 7 depicts a diagram of an example system for moving images presented to a user to diagnose and/or correct binocular vision.

FIG. 7 depicts a diagram of an example system for moving images presented to a user to diagnose and/or correct binocular vision.

The example system of FIG. 7 includes a computer system for generating images, shapes, text, pictures, animated images, videos, and/or other types of visual content. The computer system can be coupled to a visualization unit (e.g., head mounted display) to deliver an image to each eye. Based on the objective of the eye exam, the computer charts can be modified in size, color, animation, position, send selected image to each eye on the head mounted display that the patient is wearing. For example, during a diagnostics test, the patient's perception of the image seen through the visualization unit is determined (e.g., automatically or through an interview). Based on the patient's initial perception, the images can be modified and/or adjusted in position/attribute. The computer system is typically used for image modification and/or repositioning although other devices/methods, including, via a portable device, portable phone, PDA, etc. can be used as well.

In one embodiment, an objective diagnosis is performed. For example, the user adjusts the images presented through the visualization unit until the two images are perceived as one. The supervisor (e.g., eye examiner) can observe the adjustments and confirm the result or make further adjustments. Based on the adjustments, the degree of binocular vision can be determined.

In one embodiment, vision training is performed via the example system of FIG. 7. For example, two images that are modifiable in size, color, animation, position are presented to each eye on the visualization unit that the user is wearing. The training session may begin when the user perceives a single binocular image resulting from the fusion of the two images. For example, simultaneous displacement of the two images from or toward each other would facilitate development of the fusion capability of the user eyes for perceiving the two images as one image while they physically move away from each other.

The computer system can be used (e.g., by the user, eye examiner, supervisor, parent, etc.) to view, interact and record the result. The result can be saved on the computer for each eye examination session. Before each session, the previous results can be reviewed to automatically start a new diagnostic session and/or training session based on the previous results and/or the level of progress. In some embodiments, diagnosis and/or vision training can be performed over a network (e.g., using wired and/or wireless Internet connections), for example, from home and/or work performing everyday tasks. The result can be viewed and/or sent to the eye care professional. The eye charts, image and other characteristic of the test can be modified remotely by the eye care provider during the session.

Figure 8:
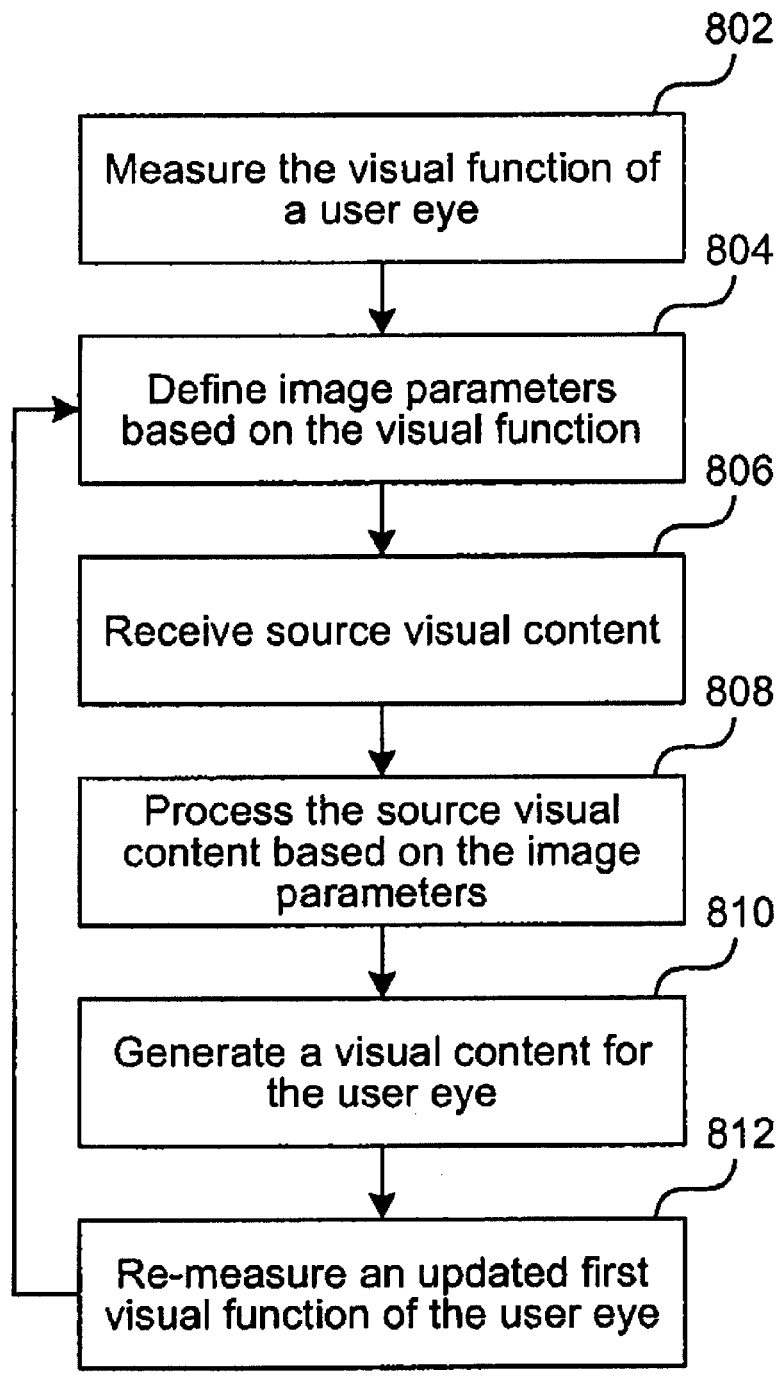
FIG. 8 depicts a flow chart illustrating an example of a process for modifying visual content to facilitate amblyopia treatment and/or correction.

FIG. 8 depicts a flow chart illustrating an example of a process for modifying visual content to facilitate amblyopia treatment and/or correction.

In process 802, visual function of a user eye is measured. The visual function of the user eye can be measured via one or more vision assessment techniques, such as, pupil dilation, hand-held slit lamp examination, ophthalmoscope examination of the retina, macula, and/or optic nerve, electroretinogram (ERG), and/or visual evoked potential (VEP), etc. The techniques can facilitate determination of visual functions including, visual acuity, contrast sensitivity, spatial frequency, contour and edge detection capabilities, stereovision, and/or orientation discrimination abilities. Typically, the first measurement is performed as a pre-evaluation of the user eye. The pre-evaluation can be used to define the image parameters to be used in a visual therapy session.

In process 804, image parameters are defined based on the measured visual function. Image parameters include, by way of example, but not limitation, contrast, brightness, color (e.g., color map, color depth, color adjustments), spatial frequency, sharpness, size, noise, motion, special effects, and/or orientation of an image and/or video. Typically, enhancement of a particular image parameter is defined when the user eye has a deficiency in the particular function. For example, if the user eye has a deficiency in detecting edges, an edge enhancement parameter can be generated. The value of the enhancement parameter is typically proportional to the degree of deficiency. Similarly, if a user eye is un-affected and functional, a reduction in image parameter is generated, in proportion to the visual strength.

In process 806, source visual content is received. The source visual content can be internally generated or received from an external source, for example, via a video connector. The source visual content can also be received wirelessly via a wireless connection to an external source (e.g., server, database, computer, etc.).

In process 808, the source visual content is processed based on the image parameters. Image processing procedures can be performed on the source visual content. The image parameters reflect the degree of visual deficit or the degree of visual strength. Typically, the image parameters yield an enhanced image for deficient eyes and reduced images for un-affected eyes. In some embodiments, the quantification of the enhancement parameters are proportional to the degree of deficiency and the quantification of the reduction parameters are proportional to the degree of strength. In process 810, visual content is generated for the user eye for which the measurement of visual function was performed. The visual content can be delivered to the user eye via a visualization device. The visual content delivered for the other eye may undergo different processing techniques and/or be processed with different values of image parameters, depending on the measured visual functions of the other eye. Typically, the visualization device can present different visual content to each eye.

In process 812, an updated visual function of the user eye is re-measured. Since eye functions may improve during therapy, visual functions can be re-measured periodically to suitably adjust the image by adjusting the image parameters suitable for the user's eye conditions. The re-measurement can be performed automatically at predetermined intervals or triggered manually.

Figure 9:
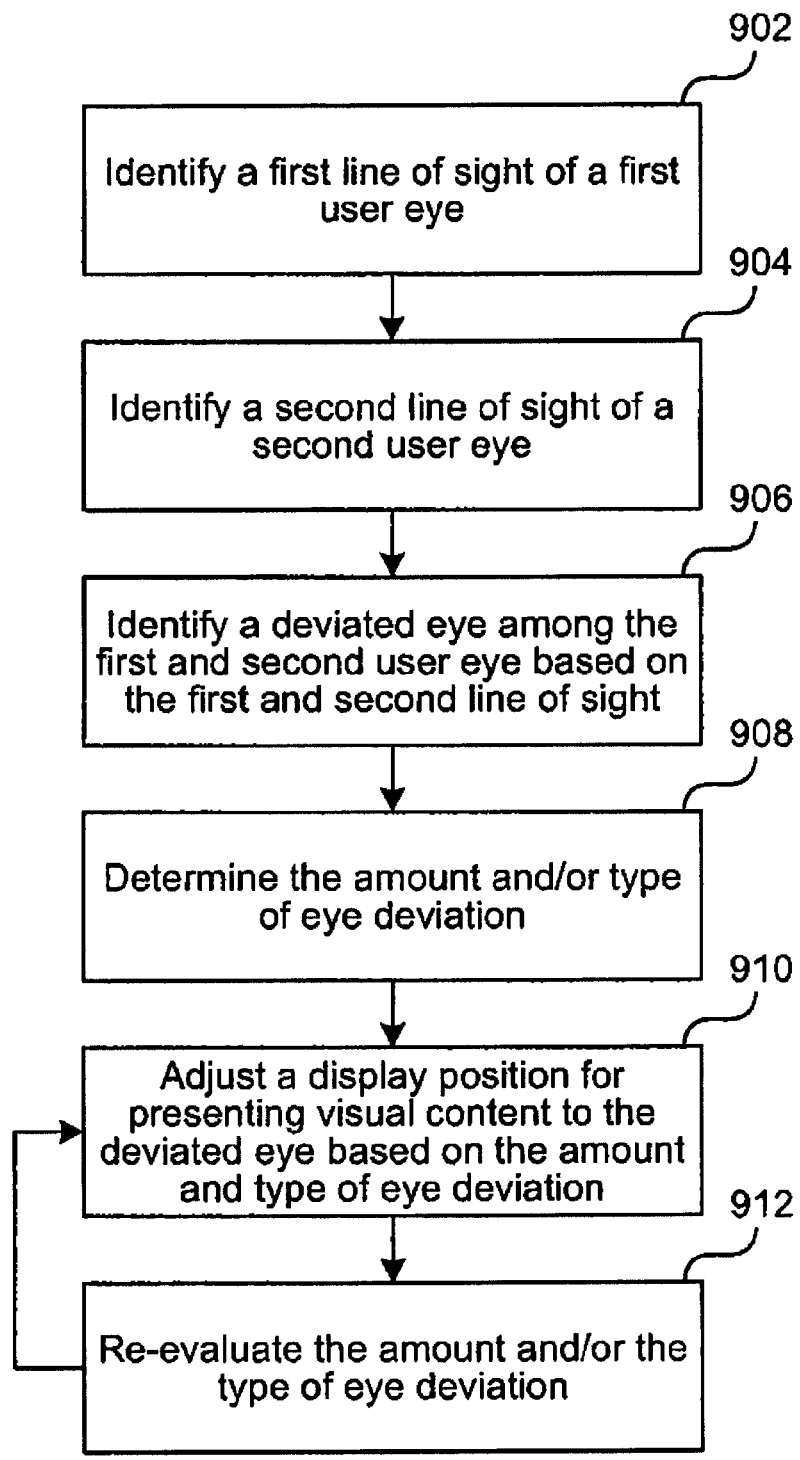
FIG. 9 depicts a flow chart illustrating an example of a process for adjusting a display/lens position to facilitate ocular deviation treatment and/or correction.

FIG. 9 depicts a flow chart illustrating an example of a process for adjusting a display/lens position to facilitate ocular deviation treatment and/or correction.

In process 902, a first line of sight of a first user eye is identified. In process 904, a second line of sight of a second user eye is identified. In process 906, a deviated eye among the first and second user eyes is identified based on the first and second line of sight. For example, if the first and second lines of sight are misaligned, one of the eyes is deviated. In other embodiments, a predetermined axis is used for determination of eye deviation. Thus, each line of sight can be compared to the predetermined axis where misalignment from the predetermined axis would indicate deviation of the eye.

In process 908, the amount and/or type of eye deviation are determined. Types of eye deviation include, horizontal, vertical, rotational, and/or tilt deviation. The amount of each type of deviation can also be determined to facilitate determination of the quantity of position adjustment of the display and/or lens. In process 910, a display position for presenting visual content to the deviated eye is adjusted based on the amount and/or type of eye deviation. Typically, the position and/or orientation of the display are adjusted such that the line of sight of the deviated eye is aligned with the center of the display. In one embodiment, a lens that is optically coupled to the display is also adjusted in position and/or orientation.

In process 912, the amount and/or type of eye deviation is re-evaluated. Since the deviated eye may gradually demonstrate migration to the un-deviated position, re-evaluation during therapy is performed for readjustment of the display and/or lens position and/or orientation to ensure alignment of the improved eye with the display and/or lens. The re-evaluation can be performed automatically at predetermined intervals or triggered manually.

Figure 10:
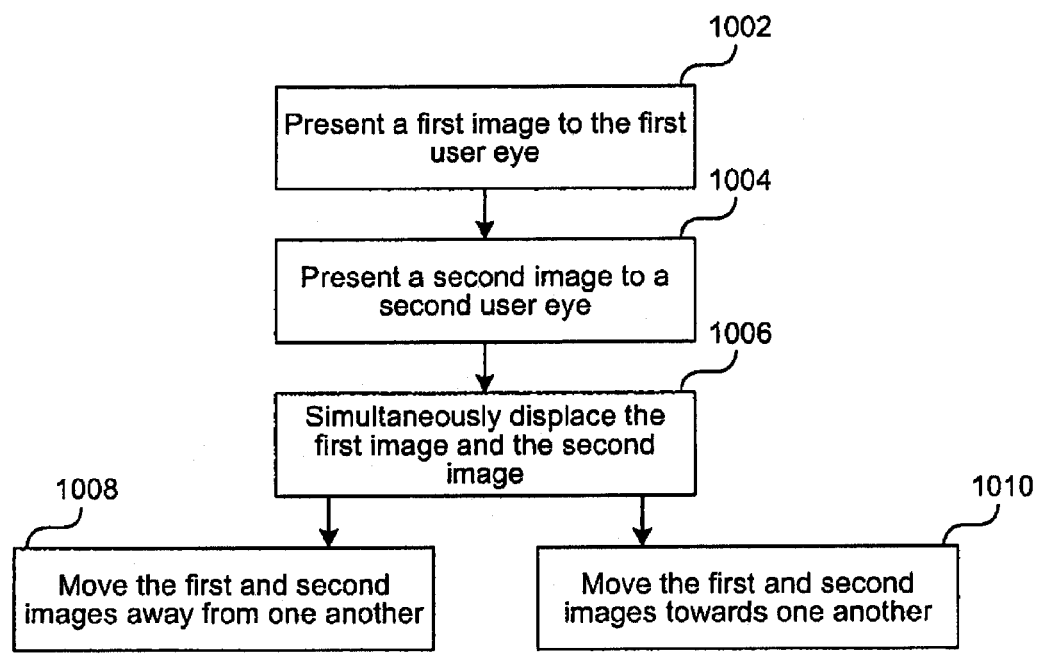
FIG. 10 depicts a flow chart illustrating an example of a process for moving two images presented to each eye of a user to facilitate binocular vision treatment and/or correction.

FIG. 10 depicts a flow chart illustrating an example of a process for moving two images presented to each eye of a user to facilitate binocular vision treatment and/or correction.

In process 1002, a first image is presented to the first user eye. In process 1004, a second image is presented to a second user eye. Images refer to any visual content including pictures, still images, moving images, animations, and/or videos (streaming and/or still). The images can be provided from a visual content source, including but not limited to, a television, a media source (e.g., DVD, VCD, BluRay, HD-DVD, etc.), a camera, a camcorder, a portable phone with imaging capabilities, etc. In one embodiment, user perception of the two images is determined. If the user has binocular vision, the image positions are initially adjusted in position and/or attributes such that the user perceives the two images as one. To proceed with training visual capabilities to fuse two images presented to two eyes of a user, in process 1006, the first and second images are displaced simultaneously from one another. For example, the images can be moved away from one another, according to process 1008. The images can also be moved towards one another, according to process 1010.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above detailed description of embodiments of the disclosure is not intended to be exhaustive or to limit the teachings to the precise form disclosed above. While specific embodiments of, and examples for, the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times. Further any specific numbers noted herein are only examples: alternative implementations may employ differing values or ranges.

The teachings of the disclosure provided herein can be applied to other systems, not necessarily the system described above. The elements and acts of the various embodiments described above can be combined to provide further embodiments.

Any patents and applications and other references noted above, including any that may be listed in accompanying filing papers, are incorporated herein by reference. Aspects of the disclosure can be modified, if necessary, to employ the systems, functions, and concepts of the various references described above to provide yet further embodiments of the disclosure.

These and other changes can be made to the disclosure in light of the above Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. 0112, sixth paragraph, other aspects may likewise be embodied as a means-plus-function claim, or in other forms, such as being embodied in a computer-readable medium. (Any claims intended to be treated under 35 U.S.C. §112, ¶6 will begin with the words "means for".) Accordingly, the applicant reserves the right to add additional claims after filing the application to pursue such additional claim forms for other aspects of the disclosure.

What is claimed is:

1. A method of ocular deviation correction, the method comprising:
   identifying a first line of sight of a first eye of a user;
   identifying a second line of sight of a second eye of the user;
   identifying a deviated eye among the first eye and the second eye based on the first line of sight and the second line of sight;
   determining an amount and type of eye deviation of the deviated eye; and
   adjusting a position of a display for presenting visual content to the deviated eye based on the amount and type of eye deviation.

2. The method of claim 1, wherein, the adjusting the position comprises, adjusting one or more of, a horizontal position, a vertical position, a tilt orientation, and a rotational position.

3. The method of claim 1, further comprising, re-evaluating the amount and the type of eye deviation of the deviated eye.

4. The method of claim 3, further comprising, re-adjusting the position of the display based on the re-evaluated amount and type of eye deviation of the deviated eye.

5. A method of binocular vision correction, the method comprising:
presenting a first image to a first eye of a user;
presenting a second image to a second eye of the user, with the first and second images aligned in a configuration such that the first and second images form a stereoscopic image for the user; and
displacing at least one of the first image and the second image with respect to one another away from the aligned configuration.

6. The method of claim 5, further comprising, determining perception of the user of the first image and the second image.

7. The method of claim 5, further comprising, wherein the displacing comprises moving the first image and the second image away from one another.

8. The method of claim 5, wherein the displacing comprises moving the first image and the second image towards one another.

9. The method of claim 5, further comprising:
determining perception of the user of the first image and the second image;
wherein simultaneously displacing the first image and the second image includes a pattern of moving the images towards and away from one another.

10. A visual interface system, comprising:
means for identifying a first line of sight of a first eye of a user;
means for identifying a second line of sight of a second eye of the user;
means for identifying a deviated eye among the first eye and the second eye based on the first line of sight and the second line of sight;
means for determining an amount and type of eye deviation of the deviated eye; and
means for adjusting a position of a display for presenting visual content to the deviated eye based on the amount and type of eye deviation.

11. The system of claim 10, wherein, the means for adjusting the position comprises means for adjusting one or more of, a horizontal position, a vertical position, a tilt orientation, and a rotational position.

12. The system of claim 10, further comprising, means for re-evaluating the amount and the type of eye deviation of the deviated eye.

13. The system of claim 10, further comprising, means for re-adjusting the position of the display based on the re-evaluated amount and type of eye deviation of the deviated eye.

14. A visual interface system comprising:
means for presenting a first image to a first eye of a user;
means for presenting a second image to a second eye of the user, with the first and second images aligned in a configuration such that the first and second images form a stereoscopic image for the user;
means for displacing at least one of the first image and the second image with respect to one another away from the aligned configuration, the means for simultaneously displacing the first image and the second image including a) means for moving at least one of the first image and the second image away from one another, and b) means for moving at least one of the first image and the second image towards one another.

15. A method of vision correction, comprising:
determining an impairment of a visual function of at least one of a first eye of a user and a second eye of the user;
presenting first visual content to the first eye of the user, the first visual content having a first degree of visual cortical stimulation of the visual function;
presenting second visual content to the second eye of the user, the second visual content having a second degree of visual cortical stimulation of the visual function, the second degree being different from the first degree;
progressively adjusting at least one of the first and second degrees such that a difference between the first and second degrees changes.

16. The method of claim 15, wherein:
the difference between the first and second degrees comprises at least one of a group consisting of a difference in spatial frequency and a difference in contrast.

17. The method of claim 15, wherein:
the difference between the first and second degrees comprises at least one of a group consisting of geometric transformation, color correction, registration, interpolation, de-mosaicing, segmentation, image editing, image scaling, image cropping, de-convolution, edge preserving smoothing, edge enhancement, perspective correction, distortion correction, image orientation adjustment, classification, noise removal, feature extraction, and pattern recognition.

18. The method of claim 15, wherein:
the impairment comprises diminished visual function in at least one of the first and second eyes.

19. The method of claim 15, wherein:
the impairment comprises at least one of a group consisting of amblyopia and ocular deviation.

20. The method of claim 15, comprising:
progressively adjusting the at least one of the first and second degrees responsive to a change in the impairment.

21. The method of claim 15, comprising:
progressively adjusting at least one of the first and second degrees such that a difference between the first and second degrees decreases.

22. The method of claim 15, comprising:
progressively adjusting at least one of the first and second degrees such that a difference between the first and second degrees decreases responsive to a decrease in the impairment.

* * * * *